(12) United States Patent
Serra et al.

(10) Patent No.: US 8,984,143 B2
(45) Date of Patent: Mar. 17, 2015

(54) EMERGENCY INFORMATION SERVICES

(75) Inventors: Matthew A. Serra, Morristown, NJ (US); Brett Wilfred Marceau, Clinton, MA (US)

(73) Assignee: Rave Wireless, Inc., Framingham, MA (US)

( * ) Notice: Subject to any disclaimer, the term of this patent is extended or adjusted under 35 U.S.C. 154(b) by 764 days.

(21) Appl. No.: 12/894,492

(22) Filed: Sep. 30, 2010

(65) Prior Publication Data

US 2011/0258266 A1 Oct. 20, 2011

Related U.S. Application Data

(60) Provisional application No. 61/324,452, filed on Apr. 15, 2010.

(51) Int. Cl.
| | |
|---|---|
| *G06F 15/16* | (2006.01) |
| *H04W 4/22* | (2009.01) |
| *H04M 3/51* | (2006.01) |
| *H04W 76/00* | (2009.01) |
| *H04W 8/18* | (2009.01) |
| *H04W 76/02* | (2009.01) |

(52) U.S. Cl.
CPC .............. *H04W 4/22* (2013.01); *H04M 3/5116* (2013.01); *H04W 76/007* (2013.01); *H04W 8/18* (2013.01); *H04W 76/025* (2013.01)
USPC ........... 709/227; 709/200; 709/204; 709/206; 709/228; 709/238; 709/239

(58) Field of Classification Search
USPC .......... 709/204, 206, 227–228, 238–239, 200
See application file for complete search history.

(56) References Cited

U.S. PATENT DOCUMENTS

| | | | | |
|---|---|---|---|---|
| 5,903,726 | A * | 5/1999 | Donovan et al. | 709/206 |
| 6,807,564 | B1 * | 10/2004 | Zellner et al. | 709/206 |
| 7,995,998 | B2 | 8/2011 | Wright et al. | |
| 2002/0059030 | A1 | 5/2002 | Otworth et al. | |
| 2002/0072348 | A1 | 6/2002 | Wheeler et al. | |
| 2002/0087634 | A1 * | 7/2002 | Ogle et al. | 709/204 |
| 2003/0012344 | A1 * | 1/2003 | Agarwal et al. | 379/37 |
| 2003/0149526 | A1 | 8/2003 | Zhou et al. | |
| 2004/0062371 | A1 | 4/2004 | Maropis et al. | |
| 2005/0012390 | A1 * | 1/2005 | Kato et al. | 303/146 |
| 2005/0124318 | A1 | 6/2005 | Jeon | |
| 2005/0151642 | A1 | 7/2005 | Tupler et al. | |

(Continued)

OTHER PUBLICATIONS i3 Stage 3 Public Review; Sections 4.1.14-4.1.15 (p. 55-56), 4.2 (p. 57), 5.2.2.5 (p. 107-108), 5.2.3 (p. 108), 5.10 (p. 169), 5.18 (p. 178-179), 7 (p. 184-209), 8 (p. 209-212).

(Continued)

*Primary Examiner* — Edward Kim
(74) *Attorney, Agent, or Firm* — Occhiuti & Rohlicek LLP

(57) ABSTRACT

A method of communicating with a user includes receiving a call from the user via a first mode of communicating; sending, to an emergency information service, via a communications network, a request for information associated with the user; receiving, from the emergency information service, via the communications network, information characterizing more than one mode of communicating with the user; and initiating communication with the user via a second mode of communicating, the second mode of communicating included in the more than one mode of communicating with the user.

26 Claims, 6 Drawing Sheets

(56) References Cited

U.S. PATENT DOCUMENTS

| | | |
|---|---|---|
| 2005/0159132 A1 | 7/2005 | Wright et al. |
| 2005/0160183 A1 | 7/2005 | Valli et al. |
| 2005/0265326 A1* | 12/2005 | Laliberte ................ 370/389 |
| 2006/0205383 A1 | 9/2006 | Rollender |
| 2007/0121799 A1* | 5/2007 | Binning ................ 379/37 |
| 2008/0319805 A1 | 12/2008 | Burke, Jr. |
| 2009/0035740 A1 | 2/2009 | Reed et al. |
| 2009/0132366 A1 | 5/2009 | Lam et al. |
| 2009/0161837 A1* | 6/2009 | Killian et al. ................ 379/45 |
| 2009/0274145 A1* | 11/2009 | Laliberte ................ 370/352 |
| 2010/0050199 A1 | 2/2010 | Kennedy |
| 2010/0223131 A1 | 9/2010 | Scott et al. |
| 2011/0060378 A1* | 3/2011 | Tuysserkani ................ 607/5 |

OTHER PUBLICATIONS

NENA Standard for NG9-1-1 Additional Data.

* cited by examiner

EMERGENCY INFORMATION SERVICES

CROSS-REFERENCE TO RELATED APPLICATIONS

This application claims priority to U.S. Provisional Application Ser. No. 61/324,452, filed Apr. 15, 2010, and entitled "Utilizing Multiple Communications Methods to Aid an Emergency Caller," the contents of which are incorporated herein by reference.

This application is also related to U.S. application Ser. No. 12/749,600, filed Mar. 30, 2010, and entitled "Emergency Information Services," the contents of which are incorporated herein by reference.

BACKGROUND

About 250 million 9-1-1 calls are made each year in the United States. Over 50% of all 9-1-1 calls originate from mobile phones, and that percentage is expected to increase in coming years as more households eliminate their landline phones. Other modes of communications, such as Voice Over Internet Protocol (VoIP), Short-Message-Service (SMS) messaging, instant messaging, and video, are emerging as new methods for communications with 9-1-1 services.

In general, conventional 9-1-1 call handling techniques support emergency calls by allowing interaction with the caller exclusively through the communication method used to initiate the 9-1-1 call. However, as the new technologies listed above become more prevalent, citizens expect Public Service Answering Points (PSAPs) to be able to handle incoming requests from these, and other, communications technologies.

Furthermore, many individuals subscribe to multiple communications services and thus may rely on more than one communications service at any given time. Conventional 9-1-1 call handling techniques and technologies support emergency calls by interacting with a caller exclusively through the communications method used to initiate the 9-1-1 call.

SUMMARY

In the context of this disclosure, a "call" includes not only traditional wireline and wireless calls but also other forms of communication. The "caller" is anyone communicating with the 9-1-1 service via any supported communication method. While the 9-1-1 Public Service Answering Point (PSAP) is used as an example throughout this disclosure, the systems and methods described herein apply equally to other public service answering points (e.g., 3-1-1 or 4-1-1) or, more generally, to any call center capable of handling communications.

In a general aspect, a method of communicating with a user includes receiving a call from the user via a first mode of communicating; sending, to an emergency information service, via a communications network, a request for information associated with the user; receiving, from the emergency information service, via the communications network, information characterizing more than one mode of communicating with the user; and initiating communication with the user via a second mode of communicating, the second mode of communicating included in the more than one mode of communicating with the user.

Embodiments may include one or more of the following.

Initiating communication with the user via the second mode of communicating includes initiating communication with the user via the second mode of communicating while maintaining communication with the user via the first mode of communicating.

Initiating communication with the user via the second mode of communicating includes ceasing communication with the user via the first mode of communicating.

Initiating communication with the user via the second mode of communicating includes obtaining information about the user from the second mode of communicating. The obtained information includes a location of the user.

The method further includes selecting the second mode of communicating based on a request by the user.

The method further includes receiving, from the emergency information service, information characterizing the user. The information characterizing the user includes a disability of the user. The method further includes selecting the second mode of communicating based on the received information characterizing the user.

At least one of the first mode of communicating and the second mode of communicating includes text messaging. The method further includes sending a text message to the user; and receiving a delivery receipt indicative of delivery of the text message to the user.

In another general aspect, a method for providing data associated with a user to an emergency service provider includes accepting, via a communications network linked to an emergency information service, information characterizing more than one mode of communicating with a user; maintaining, in a user profile module of the emergency information service, a user profile database including the information characterizing the more than one mode of communicating with the user; receiving from the emergency service provider, via the communications network, a request for information associated with the user, the request for information including an identifier of a first mode of communicating with the user, wherein a communication session between the emergency service provider and the user is ongoing via the first mode of communicating with the user when the request for information is received from the emergency service provider; and providing to the emergency service provider, via the communications network, the information characterizing the more than one mode of communicating with the user.

Embodiments may include one or more of the following.

The information characterizing the more than one mode of communicating with the user includes information indicative of the user's preferred mode of communicating.

The method includes accepting information characterizing the user; and maintaining the information characterizing the user in the user profile database. The information characterizing the user includes a disability of the user.

Accepting information characterizing more than one mode of communicating with the user includes accepting information from at least one of the user, a communications service provider associated with the user, and a third party data source.

The request for information associated with the user includes an identifier of an initial mode of communicating with the user. The initial mode of communicating with the user was used by the user to contact the emergency service provider. The method further includes accessing, in the user profile database, the information characterizing the more than one mode of communicating with the user based on the received identifier of the initial mode of communicating with the user.

The more than one mode of communicating with the user can be used serially or in parallel to communicate with the user.

In another general aspect, a method includes maintaining, in a user profile module of an emergency information service, a user profile database including information characterizing more than one mode of communicating with a user; receiving, via a communications network, a request for information associated with the user from an emergency service provider, the request for information including an identifier of an initial mode of communicating with the user; storing, in a call log module of the emergency information service, the received identifier; providing to the emergency service provider, via the communications network, the information characterizing the more than one mode of communicating with the user; monitoring communication between the emergency service provider and the user, including identifying each mode of communicating with the user utilized for communication between the emergency service provider and the user; and, for each utilized mode of communicating with the user, storing, in the call log module, an identifier of the utilized mode of communicating with the user.

Embodiments may include one or more of the following.

The method further includes receiving, from a requestor, a request for a history of communications between the emergency service provider and the user. The method further includes providing to the requestor the identifiers of each utilized mode of communicating with the user. Sending a text message to the user includes selecting a text message from a predetermined selection of standard text messages.

The systems and methods described herein have a number of advantages. For instance, using the emergency information service described herein, a PSAP operator can readily mix-and-match a caller's various communications services to maximize the options and capabilities available to assist the caller. Thus, for example, a PSAP operator can communicate with a caller over multiple communications methods to obtain information about alternate available communications methods, switch between the caller's communications methods mid-call, and simultaneously leverage the capabilities of multiple communications methods or devices associated with the caller.

This flexibility in the selection of communications methods allows the PSAP operator to more efficiently address the caller's needs. For instance, if a caller places a call via a wireline phone, the operator may be able to identify and to leverage other communications methods that are better suited to the caller's immediate needs. Thus, a user who is hard of hearing may initiate a request for assistance via a landline phone, even though SMS, Video, or Instant Messaging would allow for more efficient communications with the caller. Similarly, a caller's other communications methods may provide unique and valuable capabilities unavailable to the communications method used to place the 9-1-1 call. For example, a request for assistance placed via Instant Messaging could be further enhanced by allowing the PSAP to query the location of the caller's mobile phone to identify where the caller may be located.

The emergency information service described herein also simplifies the process for obtaining additional information from a caller (e.g., alternate contact information or location information). In conventional 9-1-1 systems, the first responder has to verbally obtain such information from the caller. If the caller is unable to respond to the first responder's inquiries, it may be difficult or impossible for the first responder to determine the identity of the caller, or the nature or location of the emergency. With the emergency information service described herein, information such as alternate contact information may be stored in a database and thus can be made readily accessible to PSAP operators and first responders. Other information, such as the location of the caller, may be retrievable without cooperation from the caller by accessing another of the caller's registered communications devices (e.g., the caller's mobile phone).

By understanding the relationship between an individual or location, and all communications methods available to the individual or location, it is possible to trace multiple independent communications sessions back to the individual placing the request for assistance (regardless of whether the caller or the PSAP initiated a call over a given communications method). Thus, each call can be viewed in context rather than as a stand-alone event.

Understanding the multiple, distinct communications events related to a request for emergency assistance, and their associated content is a valuable tool which can support investigations, audit, quality assurance, and training activates to further public safety initiatives.

Other features and advantages of the invention are apparent from the following description and from the claims.

DETAILED DESCRIPTION

Figure 1:
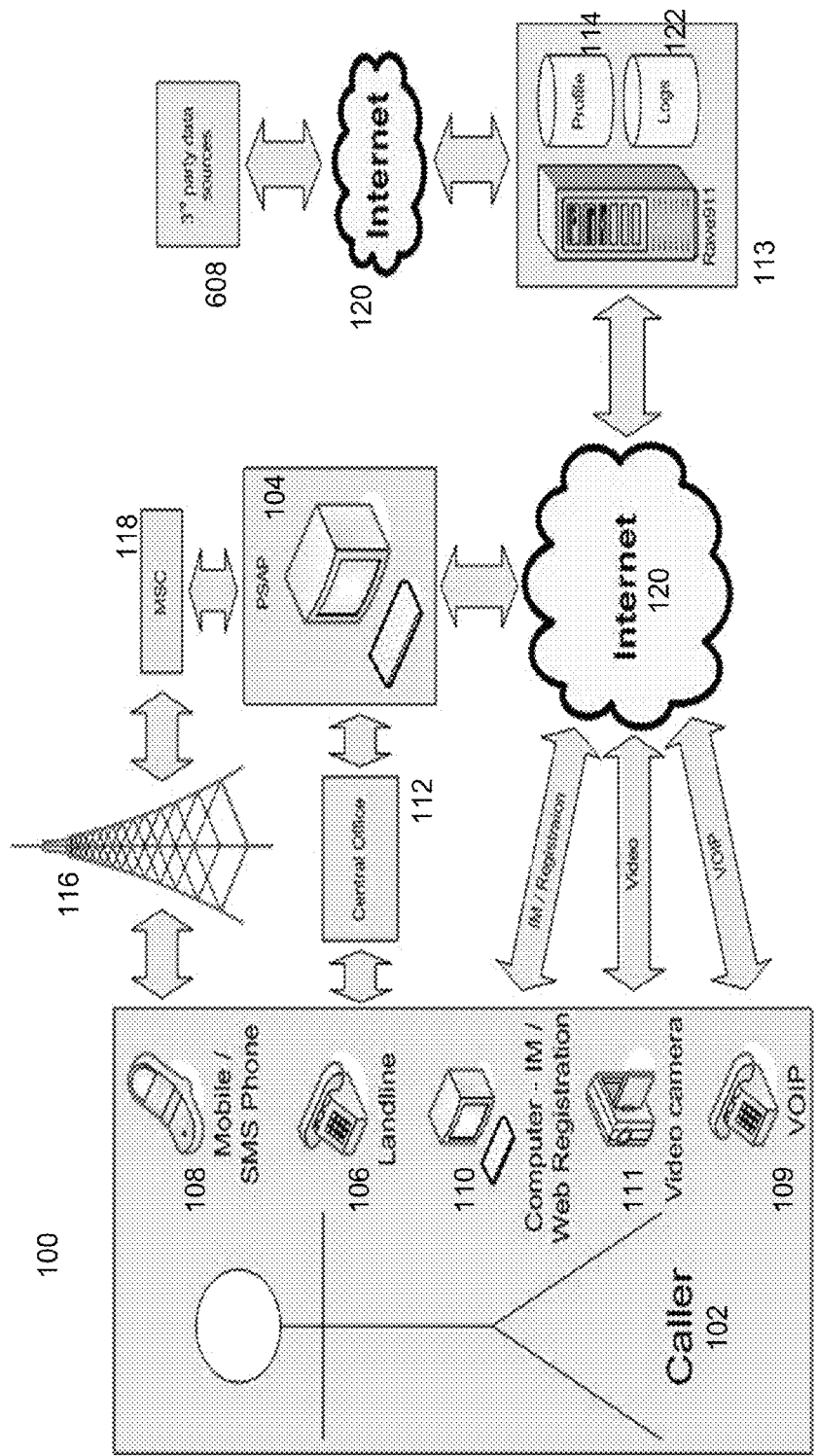
FIG. 1 is a block diagram of an emergency information system.

Referring to FIG. 1, in general, an emergency information system 100 facilitates communication between a caller 102 and a Public Service Answering Point (PSAP) 104. Caller 102 initiates communication with PSAP 104 (i.e., places a request for emergency assistance) via a mode of communication, such as a call from a landline phone 106, a call from a mobile phone 108, a Voice over Internet Protocol (VoIP) service 109, a short-message-service (SMS) message using mobile phone 108, an instant message (IM) using a computer 110, or a video call using a video camera 111.

An emergency information service 113 augments the data and communications options available to PSAP 104 and/or first responders by providing these entities with access to a subscriber profile database 114 based on the caller's phone number or other unique identifier (e.g., an IM name). In some cases, database 114 is a single national database. In other cases, data is dynamically referenced in multiple databases. Alternatively, database 114 is local to the caller's calling device. For instance, the caller's mobile phone may have an application that stores, local to the phone itself, information about the caller and the caller's other contact devices. In a Next-Generation 9-1-1 environment, the caller information stored in the local database is delivered to the network as an accompaniment to the 9-1-1 call.

Database 114 stores information about the caller's available communications methods and devices. Database 114 may also describe the capabilities of the caller's communication services and the caller's preferences related to the use of his various communications devices. In some cases, the database may also include information characterizing disabilities or other special needs which may affect the caller's ability to communicate.

Emergency information service 113 provides a way for PSAP 104 or a first responder to switch between or to simultaneously access the caller's communications services or devices. The emergency information system also provides a way to associate information about communications services or devices with a particular caller(s) and/or a particular location(s).

In some embodiments, the caller himself can identify the presence or relevancy of an alternate communications device during communication with the PSAP or first responder or immediately upon placing the request for emergency assistance. Emergency information service 113 includes several aspects, each of which can be deployed as a separate component or in conjunction with one or more of the other components. These aspects, which are discussed in more detail below, include:

- Collection of caller-specific information identifying the caller's available communications services and devices, address(es), phone number(s), communications preferences, and/or disabilities or other special needs;
- Maintaining the above information up-to-date;
- Processing and responding to real-time requests from a PSAP or first responder for the caller's available communications service and/or device inventory and associated information;
- Viewing the caller's communications services, devices, and preferences; and the caller's disabilities or special needs; and switching between or simultaneously utilizing multiple of the available services and/or devices; and
- Associating all communications methods used to support a given request for emergency services.

1 Collection of Caller-Specific Information

Emergency information service 113 is a subscription-based service that collects and stores information about registered users in database 114. During registration with the emergency information service, subscriber data is collected through third parties such as communications service providers or; subscriber facing computer interfaces, such as web sites and Interactive Voice Response (IVR) systems. In some cases, additional data may be provided to emergency information service 113 by the device or communication service in real-time with an inbound call. Subscriber data is associated with the subscriber, the subscriber's physical address(es), other people in the subscriber's household, and other people or organizations with whom the subscriber is affiliated, such as a business, family, or social organization. These associations are maintained within or managed by the emergency information service database(s).

In some instances, a subscriber can confirm ownership of and describe communications methods, devices, capabilities, and preferences through other data-stores that manage such data. These other data-stores subsequently release this information to the emergency information service 113. Subscribers can also register or append their information to existing profiles directly through interfaces managed by the emergency information service, such as a web application, a mobile interface (e.g., web enabled, multimedia messaging service (MMS), or SMS), an IVR system, or an IP based protocol, such as Session Initiation Protocol (SIP).

The database of the emergency information service also maintains data characterizing the capabilities of each registered communications device. For instance, the database may include information such as which of the registered device(s) or service(s) are capable of communicating via particular method(s) and/or are capable of providing an advanced service such as an identification of a caller's location. Information about device and service capabilities may be provided during each subscriber's registration with the emergency information system service. Alternatively, such information may be provided in real-time during a caller's interaction with the PSAP or first responder via self-description by the device.

By associating multiple devices or services with a caller, with an address, or through relationships the caller has with other people, the PSAP operator or first responder responding to a call through a registered communications device can be presented with alternate methods for communicating with the caller. Furthermore, based on the caller's limitations (e.g., hearing impairment, sight impairment, etc) as identified previously (e.g., during registration), and/or his communications preferences (e.g., mobile vs. fixed telephone; text vs. audio vs. video; etc.) the PSAP operator or first responder can make an informed decision about which communications method is best suited to address the caller's needs and, if appropriate, switch to a different communications method to continue the interaction with the caller.

A registered caller may also augment information in the database about his communications services and/or devices in real-time. For example, the caller may interact with the device's user-interface, or with an application in the PSAP or communications provider network, to indicate he wishes to be contacted via an alternate communications method. For example, a caller may initially place a voice call to 9-1-1 but then realize that speaking to the PSAP operator might further provoke an assailant. In this case, the caller could indicate that continuing the interaction with the PSAP operator via a text-based alternative would be preferable.

In some embodiments, the emergency information service offers different subscription levels, each level allowing a different amount of information to be maintained. For example, the service could support basic and premium models where certain information is included in the basic service and other information is only available with a premium fee or purchase of an additional module.

2 Maintaining Up-to-Date Information

A subscriber's communications methods, devices, capabilities, and preferences may change frequently. For instance, a subscriber may obtain a new communications method (e.g., subscribing to a VoIP service) or device (e.g., purchasing a new mobile phone or upgrading to a smartphone with expanded capabilities). As another example, if a subscriber is associated with a business, the profile of communications methods or devices available at the location of the business may change if the business upgrades its communications service.

The emergency information service provides service providers (e.g, mobile phone service providers) and individual subscribers with the ability to identify the addition or removal of devices or communications methods and capabilities. In addition, the emergency information service provides the ability for service providers and individual subscribers to identify their own communications limitations, capabilities, and/or preferences. In some embodiments, the emergency information service provides processes that allow for automatic or self-reported updates of devices or device capabilities based on the use of a device by an individual, or based on an upgrade or downgrade of services associated with a previously registered device or communications method.

In some embodiments, subscribers to the emergency information service are proactively prompted to update their information, e.g., at predetermined time intervals. This update prompt could be sent via email, SMS, instant message, or any other communications method registered to the subscriber. Alternatively, the update prompt could be provided through messages from a communications service provider or via touch points of other affiliated third parties (e.g., a printed bill, a customer support web site, federal/state/municipal websites, etc).

3 Processing Real-Time Requests

Upon receiving a 9-1-1 call, a PSAP operator or first responder can use information about the inbound call to query the emergency information service in order to identify other communication methods associated with the inbound communication method or user. The emergency information service returns a response to the PSAP operator or first responder that may also include a listing of the capabilities of each registered method (e.g., audio, text, video, location, presence, etc) associated with the caller, the caller's relative preference for each method, and the availability or location of each method. The preference ranking may also include information about the limitations of the caller (e.g., hearing impaired) which would also allow the emergency responder to make an informed decision about which communications method would be best suited to the situation.

Through the emergency information service, the emergency responder can select an alternate communications method from a list of options and continue the conversation with the caller across the selected channel. This conversion between communications methods could include "serially" conducting the conversation, where the prior method is abandoned, and the new method used exclusively, or conducting the conversation in "parallel" conversation, in which the conversation is carried forward across both the original communications method and each new communications method.

As an example of "serial" communication, a caller may initiate a 9-1-1 call via a mobile phone. The first responder may recognize that the call would be better handled by switching over to the caller's landline phone.

As an example of "parallel" communication, a caller may initiate a 9-1-1 call via Instant Messaging. The first responder may find it valuable to augment the text-based conversation by listening into what is happening at the caller's location. In this case, the first responder would place a call to the caller's mobile phone, while retaining the initial contact via the Instant Messaging session.

In yet another example of "parallel" communication, a caller may initiate a 9-1-1 call via an Instant Messaging session. The first responder may choose to utilize the location capabilities of the mobile device registered within the caller's Rave911 account to determine the caller's location while continuing to communicate with the caller via IM.

In some cases, the emergency information service can also provide information about communications methods, devices, and preferences associated with other users affiliated with the caller. For example, if a first responder is not able to contact the caller making the request for assistance via an alternate communications method, the caller's registered preferences and contact information may direct the first responder to contact another individual, such as a parent or guardian.

The query for information about alternate communications methods may be issued against a database local to the PSAP, or over the Internet or another remote network to a distributed database hosted and managed outside of the PSAP.

The query for information about alternate communications methods, and the resulting initiation of the communications session, may be issued from distinct computer systems or software, or all functions may be consolidated within a single user interface, or a combination of these approaches may be employed.

In some instances, when the caller communicates with the PSAP operator via SMS, a delivery receipt is displayed in the PSAP operator's user interface, so that the operator can confirm that the caller received the text message sent from the PSAP. In other instances, the PSAP operator's SMS chat window is prepopulated with a selection of "canned" responses that are often used in emergency situations (e.g., "Where are you" or "Is anyone injured"). These canned responses may be selected by the operator based on the operator's own professional experience and judgment or may be preselected by the emergency information service based on the nature of the caller's emergency.

4 Logging the Aggregated Communications Event

By understanding the relationship between an individual or location, and all communications methods available to the individual or location, it is possible to trace multiple independent communications sessions back to the individual placing the request for assistance (regardless of whether the caller or the PSAP initiated a call over a given communications method). Thus, each call can be viewed in context rather than as a stand-alone event.

The emergency information service described above enables this capability. In one embodiment, the information returned by the query for Communications Method Information can be used to discover the relationships between multiple communications methods, enabling logging of related events. In another embodiment, the act of leveraging the emergency information service to discover relationships among calls, and to manage some or all subsequent communications, allows for such relationships to be discovered and logged.

Understanding the multiple, distinct communications events related to a request for emergency assistance, and their associated content is a valuable tool which can support investigations, audit, quality assurance, and training activates to further public safety initiatives.

5 Examples

The following examples demonstrate how the emergency information system stores, manages, and makes information available about a subscriber's communications methods, preferences, and disabilities in order to best address the caller's needs. While specific communications methods are provided in these examples, any combination of voice, video, text based, or telematics services can be supported via the emergency information service. In general, communications may be initiated by either the caller, or by the PSAP operator.

5.1 Inbound Call with Serial Communications

Figure 2:
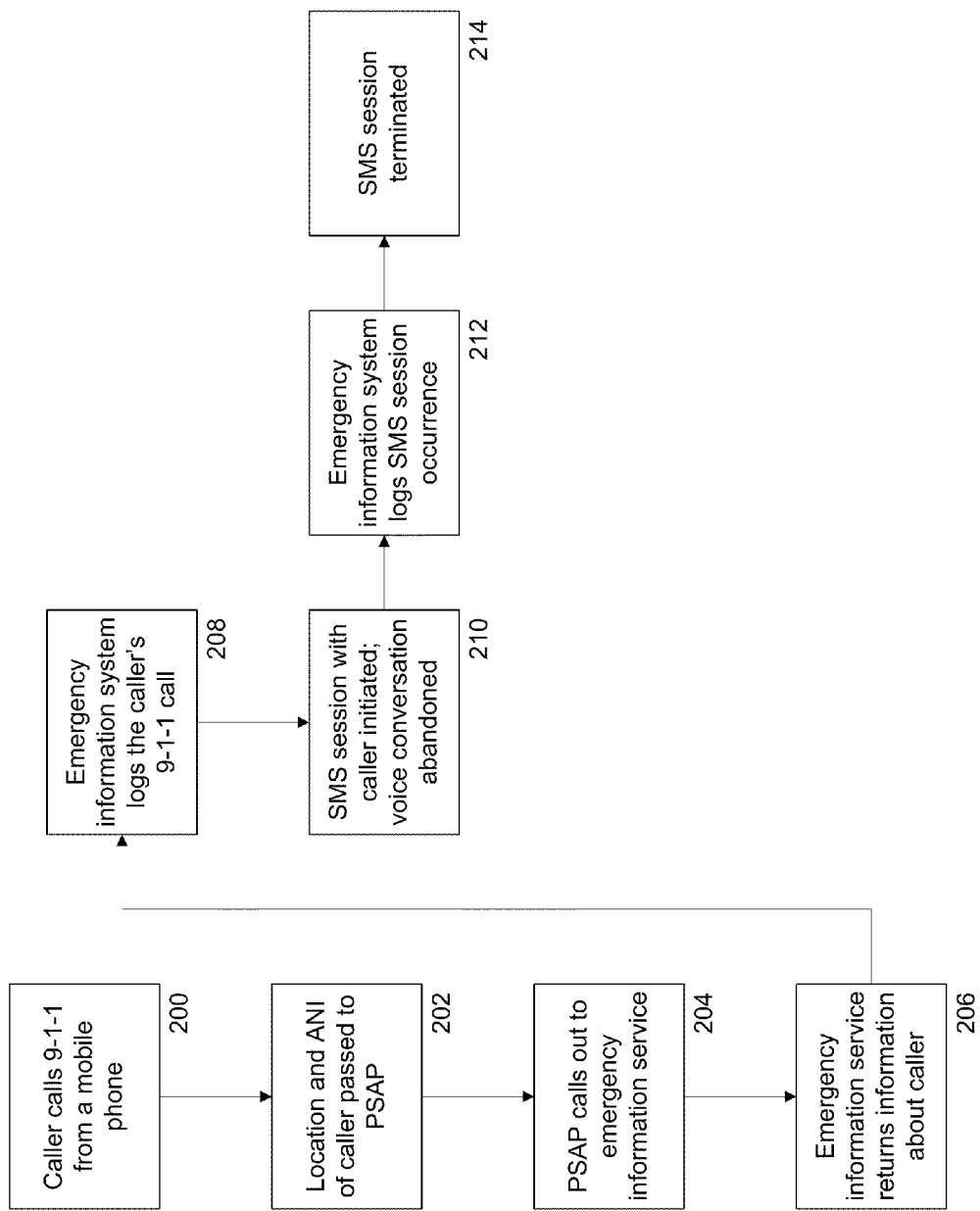
FIG. 2 is a flow chart for an inbound call with serial communications.

Referring to FIGS. 1 and 2, in one example, when a subscribed caller 102 calls 9-1-1 via a mobile phone 108, the call connects to a wireless tower 116 and is routed to a Mobile Switching Center (MSC) 118 (step 200). Based on the location of the mobile phone 108, an appropriate PSAP 104 is identified.

The location and Automatic Number Identification (ANI) of caller 102 are passed to the PSAP 104 (step 202). The location is populated in an Automatic Location Identification (ALI database), where a computer-aided dispatch (CAD) system or other end user system queries the database for the location and then displays it visually for the PSAP operator.

Concurrent with the ALI database query, the CAD system calls out to emergency information service 113 (step 204) via the Internet 120 or another network. Based on the identity of the caller, the emergency information service accesses the caller's information in a subscriber profile database 114 and returns information about the caller and his associated communications services to PSAP 104 (step 206). The data may be presented embedded within the CAD system in use at the PSAP or may be presented in a separate application. Simultaneously, the emergency information service logs the event in a log 122 (step 208), noting that the caller initiated a request for assistance via his mobile phone.

The caller communications services data returned by emergency information system 113 may include communication options, preferences, and caller disabilities. The PSAP operator can use this information to determine if a different mode of communication is more appropriate. For example, the PSAP operator may realize caller 102 is hearing impaired, and will initiate an SMS session via mobile phone 108 with the caller and abandon the voice-based mobile phone conversation (step 210). Once the SMS session has begun, the operator will continue to communicate and assist the caller through this newly established channel.

Emergency information system 113 updates logs 122 (step 212) to note that the mobile call was terminated and an SMS session was initiated for the user. This history is also available to the PSAP operator throughout the call.

Upon addressing the caller's needs, the PSAP operator terminates the SMS session (step 214).

At a later time, another PSAP operator may need to retrieve information about all communications used to support a particular incident. The emergency information service logs 212 can be queried by incident or by caller identifier to retrieve this information. The resulting history is returned to the PSAP.

5.2 Inbound Call with Parallel Communications

Figure 3:
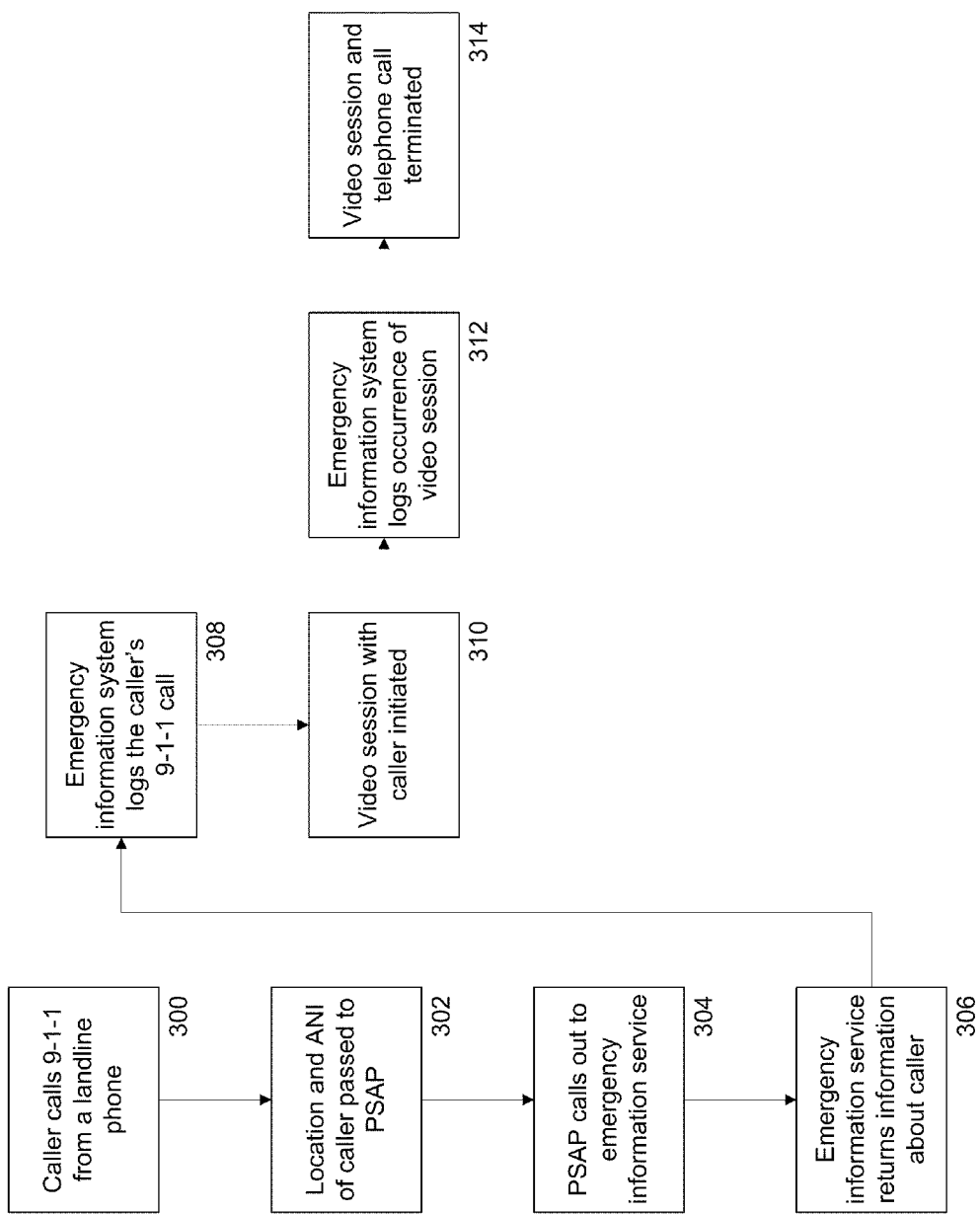
FIG. 3 is a flow chart for an inbound call with parallel communications.

Referring to FIGS. 1 and 3, in another example, caller 102 uses a landline phone 106 to initiate a request for assistance (step 300). This call is routed through the caller's switched circuit network 112, which accesses databases to determine which PSAP should receive the call.

The call and the subscriber ANI is passed to the appropriate PSAP 104 (step 302). The ANI is used to query the caller's address from within the ALI database, which is then displayed visually to the PSAP operator via the CAD system or another end user system.

Concurrent with the ALI database query, the CAD or other supporting system calls out to emergency information service 113 (step 304). Based on the identity of the caller, the emergency information service accesses the caller's information in the subscriber profile database 114 and returns information about the caller and his associated communications services to PSAP 104 (step 306). The data may be presented embedded within the CAD system in use at the PSAP or may be presented in a separate application. Simultaneously, the emergency information service logs the event in log 212 (step 308), noting that the caller initiated a request for assistance via landline phone 106.

Using the information provided by emergency information system 113, the PSAP operator recognizes that caller 102 has a registered video camera 111. The PSAP operator opens a session to view images produced by the caller's video camera (step 310).

The PSAP operator is presented with video stream from camera 111, and can continue to support the caller through the caller-initiated landline call while simultaneously viewing the caller or incident as captured by the video camera. The emergency information service logs 212 are updated to note that camera 111 was accessed to support the caller and the related incident (step 312).

Upon addressing the caller's needs, the PSAP operator terminates both the landline call and the video session (step 314).

At a later time, another PSAP operator, law enforcement officer, or other party may need to retrieve information about all communications used to support a particular incident. The emergency information service logs 212 can be queried by incident or caller identifiers to retrieve this information. The resulting history is returned to the PSAP.

5.3 Inbound Call with Parallel Device Query

Figure 4:
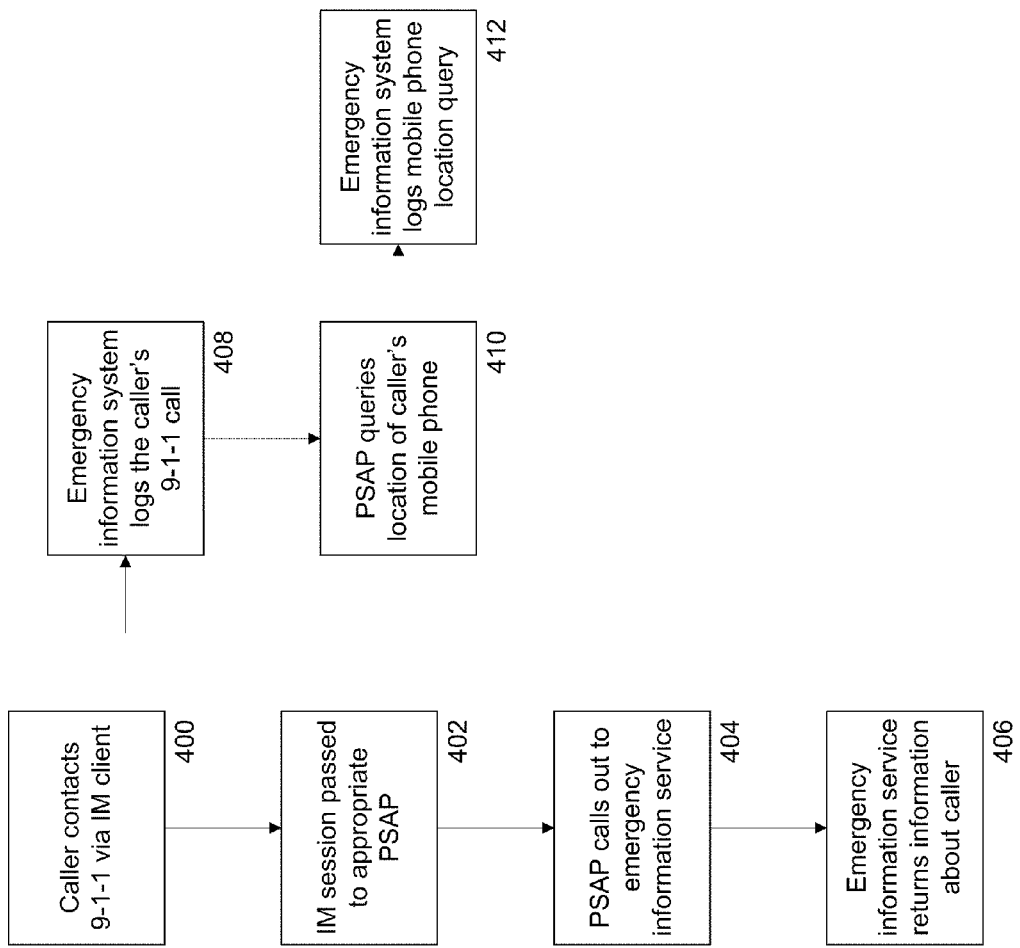
FIG. 4 is a flow chart for an inbound call with a parallel device query.

Referring to FIGS. 1 and 4, in another example, caller 102 uses an instant messenger (IM) client to initiate a request for assistance via a computer 110 (step 400).

A component within Internet 120 determines which PSAP should receive the IM session. The IM session is passed to the appropriate PSAP (step 402), where the communications are displayed to the PSAP operator within an appropriate user interface.

The PSAP CAD, or other supporting system, calls out to emergency information service 113 (step 404) and queries the subscriber profile database 114 using the caller's instant messenger ID as input. The emergency information system 113 returns all the stored information about the caller's disabilities, other communications services, and preferences, to PSAP 104 (step 406). The data may be presented embedded within the CAD system in use at the PSAP or may be presented in a separate application. Simultaneously, the emergency information service logs the event in a log 212 (step 408), noting the caller initiated a request for assistance via his IM account.

By evaluating the information returned by the emergency information service 113, the PSAP operator or supporting platform recognizes that the caller has a location-capable mobile phone 108. The PSAP operator queries the location of the mobile device (step 410). In other embodiments, the PSAP operator can query other devices registered to the caller to retrieve other communications or telematics data for each devices. The attempt to locate the mobile device is recorded within logs 212 (step 412)

The operator is presented with the location of the mobile phone, and can continue to support the caller through the user-initiated instant messenger session.

At a later time, another PSAP operator may need to retrieve information about all communications methods used to support a particular incident. The emergency information service logs 212 can be queried by incident or by caller identifiers to retrieve this information. The resulting history is returned to the PSAP.

5.4 Inbound Call with Real-time Preference

Figure 5:
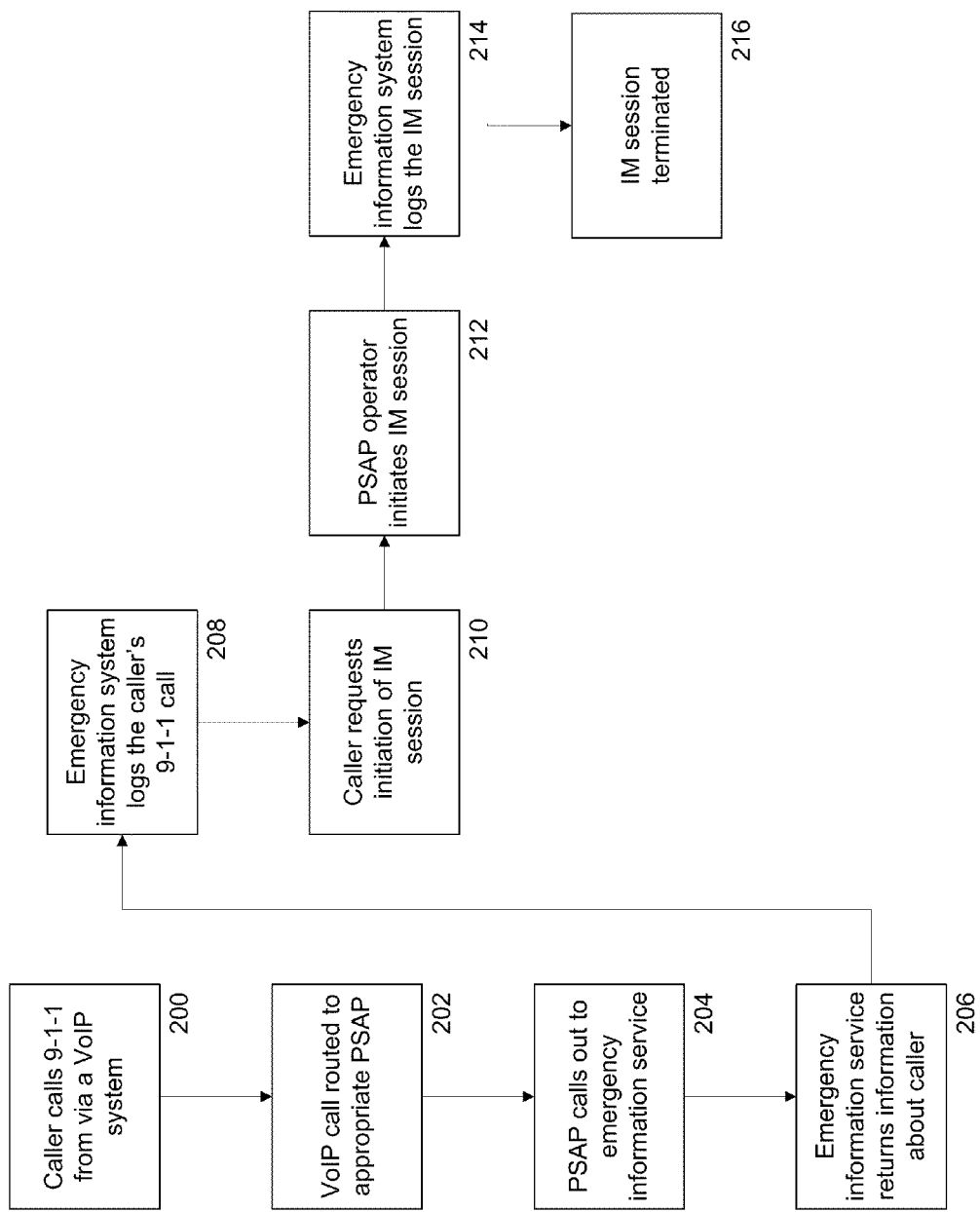
FIG. 5 is a flow chart for an inbound call in which the caller indicates a real-time device preference.

Referring to FIGS. 1 and 5, in another example, when caller 102 calls 9-1-1 (step 500) via a VoIP system 109 using a system having Next-Generation 9-1-1 (NG9-1-1) architecture, the VoIP provider recognizes the request for emergency services, and directs the Session Initiated Protocol (SIP) message for the call to the "nearest" ESInet Border Control Function (BCF).

The BCF transfers the SIP request to the "nearest" Emergency Service Routing Proxy (ESRP), which references its assigned Emergency Call Routing Function (ECRF) to determine how to route the SIP call. The ECRF is provided with the caller location information passed with the call to determine the "next hop" for the SIP request. This next hop may be another ESRP, or the destination PSAP. The ESRP uses the ECRF returned URI to direct the SIP message to its next hop. For this scenario, we assume the next hop is to a PSAP operator within the target PSAP 104 (step 502). Voice communications are initiated between caller 102 and the PSAP operator.

Based on the SIP URI or other data referenced within the SIP message, the CAD system calls out to the emergency information service 113 (step 504). Based on the query key, the emergency information service returns all the stored information about caller 102 and his associated communications services to PSAP 104 (step 506). The data may be presented embedded within the CAD system in use at the PSAP or may be presented in a separate application. Simultaneously, the emergency information service logs the event in log 212 (step 508), noting the caller initiated a request for assistance via VoIP phone 109.

During the session, caller 102 may indicate to the PSAP operator that they wish to be contacted via Instant Message (step 510), as he believe an intruder may be in his home, and he does not want the conversation to be overheard.

The PSAP operator initiates a text-based session via the Real-Time-Text (RTT) protocol, which is negotiated between the operator's user agent, the SIP infrastructure, and the caller's IM user agent (step 512). Once the IM session has begun, the operator will continue to communicate and assist the caller through this newly established channel.

The emergency information service logs 212 are updated (step 514) to note that the IM session was initiated for the caller. This history is also available to the PSAP operator throughout the call.

Upon addressing the caller's needs, the PSAP operator terminates the IM session (step 516)

At a later time, another PSAP operator may need to retrieve information about all communications used to support a particular incident. The emergency information service logs 212 may be queried by incident or caller identifiers to retrieve this information. The resulting history is returned to the PSAP.

5.5 Creation and Maintenance of Subscriber Profiles

Figure 6:
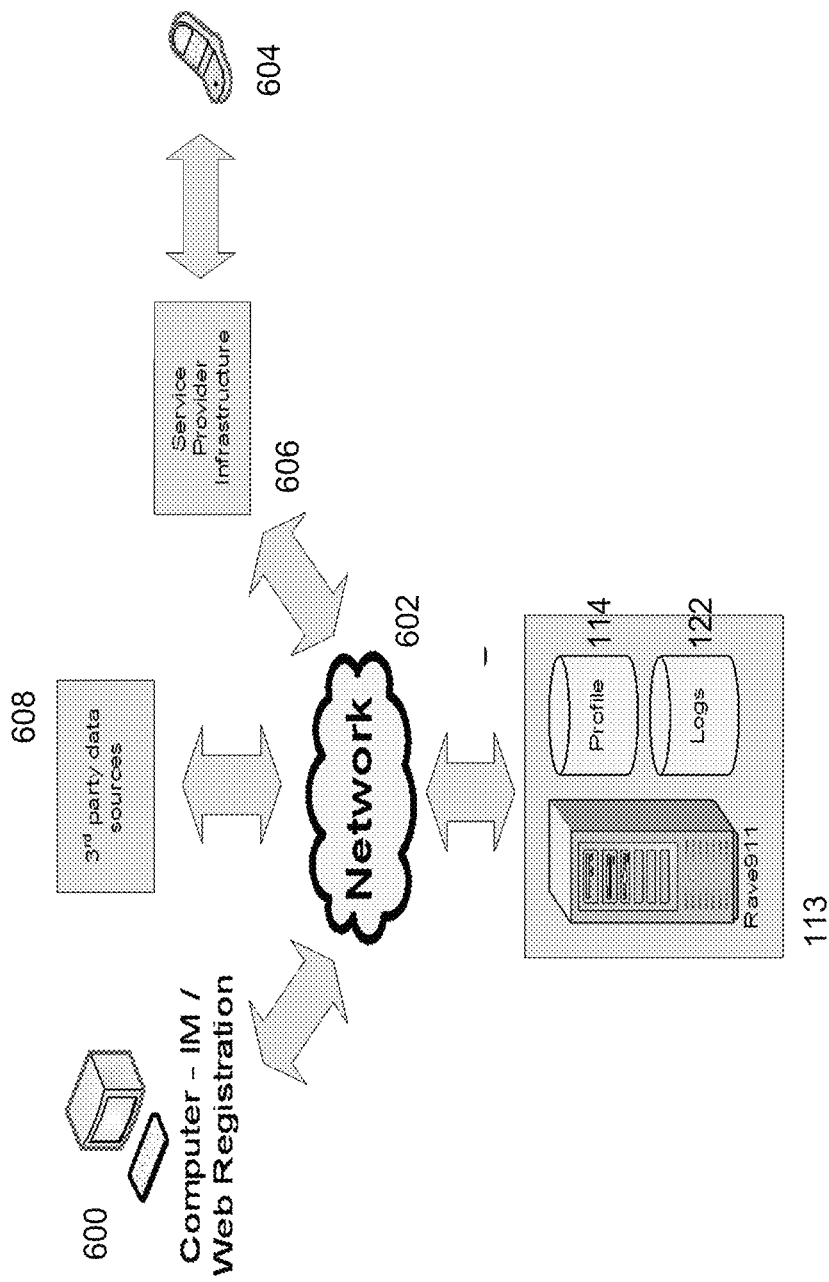
FIG. 6 is a block diagram depicting the creation and maintenance of subscriber profiles in an emergency information service.

Referring to FIG. 6, upon registration and establishment of an account with the emergency information service 113, a subscriber can register his communications devices, communications preferences, and/or disabilities or special needs with the emergency information service. The subscriber can register with and later log into the emergency information service via a computer 600 connected to a communications network 602 or a mobile phone 604 connected to communications network 602 via infrastructure 606 supported by the mobile phone service provider.

To register communications services and devices, the subscriber identifies the communications services he owns or to which he has access. The subscriber is requested to provide information sufficient to uniquely identify the service, such as the service provider, service type, and account and/or device identifying information. The subscriber may also be prompted to identify the capabilities of each device and to list his preferences for how the devices should be used for PSAP-initiated communications. Additionally, the subscriber may choose to enter any disabilities or special needs which would affect the subscriber's ability to communicate with a PSAP operator.

A Subscriber Profile is created within the subscriber profile database 114 and is populated with the user provided data described above.

Once registered, if a subscriber has a new or updated communications service or device, the subscriber logs into the emergency information service portal and identifies himself to gain access to his account. The subscriber can then modify his profile by adding new services or modifying existing services. Likewise, the subscriber can change his communications preferences or update the listing of disabilities and special needs stored by the emergency information service.

In some instances, the emergency information service may obtain information about a subscriber by contacting or being contacted by third party data sources 608, such as electronic health records, law enforcement databases, or governmental records. The emergency information service updates the subscriber's profile as appropriate based on the information obtained from these third party sources.

In some cases, a subscriber may modify an existing communications service by using the service in a unique way or by changing his arrangement (e.g., service contract) with the communications service provider. These changes may include the device or service identifier, the communications capability of the device, or the expansion or removal of relevant features. In these cases, the communications service provider recognizes this change is relevant to the subscriber's emergency information service account and sends notice of the change to the emergency information service, which updates the subscriber profile to reflect the modified service.

The techniques described herein can be implemented in digital electronic circuitry, or in computer hardware, firmware, software, or in combinations of them. The techniques can be implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps of the techniques described herein can be performed by one or more programmable processors executing a computer program to perform functions of the invention by operating on input data and generating output. Method steps can also be performed by, and apparatus of the invention can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the techniques described herein can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element, for example, by clicking a button on such a pointing device). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The techniques described herein can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an implementation of the invention, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and server are generally remote from each other and typically interact over a communication network. The relationship of client and server arises by virtue of computer programs running on the respective computers and having a client-server relationship to each other.

It is to be understood that the foregoing description is intended to illustrate and not to limit the scope of the invention, which is defined by the scope of the appended claims. Other embodiments are within the scope of the following claims.

What is claimed is:

1. A method of having an emergency-service provider establish communication with a caller who is registered with an emergency information service that maintains information concerning an alternative mode of communicating with said caller, wherein said alternative mode is an alternative process of communication, said method comprising said emergency-service provider executing steps of:
   receiving a call from said caller, wherein said call is made by said caller using a first communication mode;
   using a communication network, sending, to said emergency information service, a request for information associated with said caller;
   receiving, from said emergency information service, via said communications network, information characterizing a second communication mode for communicating with said caller, wherein said information characterizing a second communication mode for communicating with said caller includes an identifier that identifies said second communication mode;
   deciding to use said second communication mode to communicate with said caller;
   deciding whether to maintain communication with said caller using said first communication mode; and
   initiating communication with said caller via said second communication mode.

2. The method of claim 1,
   wherein deciding whether to maintain communication with said caller using said first communication mode comprises: deciding to maintain communication with said caller using said first communication mode; and
   wherein initiating communication with said caller via said second communication mode comprises: initiating communication with said caller via said second communication mode while maintaining communication with said caller via said first communication mode.

3. The method of claim 1,
   wherein deciding whether to maintain communication with said caller using said first communication mode comprises deciding to no longer maintain communication with said caller using said first communication mode; and
   wherein initiating communication with said caller via said second communication mode comprises ceasing communication with said caller via said first communication mode.

4. The method of claim 1, wherein initiating communication with said caller via said second communication mode comprises obtaining information about said caller from said second communication mode.

5. The method of claim 4, wherein said information about said caller includes a location of said caller.

6. The method of claim 1, further comprising selecting said second communication mode based on a request by said caller.

7. The method of claim 1, further comprising receiving, from said emergency information service, information characterizing said caller.

8. The method of claim 7, wherein said information characterizing said caller includes information indicative of a disability of said caller.

9. The method of claim 7, wherein said information characterizing said caller includes information indicative of an inability of said caller to maintain communication using said first communication mode.

10. The method of claim 7, further comprising selecting said second communication mode based on said information characterizing said caller.

11. The method of claim 1, wherein at least one said first communication mode and said second communication mode is text messaging.

12. The method of claim 11, further comprising sending a text message to said caller, and receiving a delivery receipt indicative of delivery of said text message to said caller.

13. The method of claim 12, wherein sending a text message to said caller includes selecting a text message from a predetermined selection of standard text messages.

14. A method for having an emergency-information service offer, to an emergency-service provider, an option to use an alternate communication mode for communication with a registered user, wherein said alternate communication mode is an alternative process of communication, said method comprising having said emergency-information service execute steps of:
   accepting, from a registered user, via a communications network linked to an emergency information service, mode information, wherein said mode information characterizes modes of communicating with said registered user;

maintaining, in a user-profile module, a user-profile database, wherein said user-profile database includes said mode information;

while a communication session between said emergency-service provider and a caller is ongoing via said first communication mode, receiving, from said emergency-service provider, via said communications network, a request for information associated with said caller, who is a registered user, wherein said request for information includes an identifier of a first communication mode for communicating with said caller;

retrieving, from a user-profile module associated with said caller, said mode information; and providing said mode information to said emergency-service provider, via said communications network to enable said emergency-service provider to determine whether to use said alternate mode of communication.

15. The method of claim 14, wherein said mode information includes information indicative of said registered user's preferred mode of communicating.

16. The method of claim 14, further comprising accepting information characterizing said registered user, and maintaining said information characterizing said registered user in said user-profile database.

17. The method of claim 16, wherein said information characterizing said registered user includes information indicative of a disability of said registered user.

18. The method of claim 16, wherein said information characterizing said registered user includes information indicative of an inability of said registered user to use said first communication mode.

19. The method of claim 14, wherein accepting mode information includes accepting information from said registered user.

20. The method of claim 14, wherein accepting mode information includes accepting information from a communications service provider associated with said registered user.

21. The method of claim 14, wherein accepting mode information includes accepting information from a third party data source.

22. The method of claim 14, wherein said request for information associated with said caller, who is a registered user, includes an identifier of an initial mode of communicating with said registered user.

23. The method of claim 22, wherein said initial mode was used by said registered user to contact said emergency-service provider.

24. The method of claim 22, further comprising accessing, in said user-profile database, said mode information based on said received identifier of said initial mode.

25. The method of claim 14, wherein said modes of communicating can be used serially to communicate with said registered user.

26. The method of claim 14, wherein modes of communicating can be used in parallel to communicate with said registered user.

* * * * *